United States Patent [19]

Nakagawa et al.

[11] Patent Number: 5,339,673
[45] Date of Patent: Aug. 23, 1994

[54] GAS CHROMATOGRAPH AND METHOD OF USING SAME

[75] Inventors: Kazuya Nakagawa; Satoru Miyoshi; Toyoaki Fukushima, all of Kyoto, Japan

[73] Assignee: Shimadzu Corporation, Kyoto, Japan

[21] Appl. No.: 34,676

[22] Filed: Mar. 19, 1993

[30] Foreign Application Priority Data

Apr. 6, 1992 [JP] Japan .................. 4-114159

[51] Int. Cl.⁵ .................................. G01N 30/10
[52] U.S. Cl. .......................... 73/23.36; 73/23.42
[58] Field of Search .................... 73/23.36, 23.42

[56] References Cited

U.S. PATENT DOCUMENTS 4,962,662 10/1990 Berger ........................... 73/23.42
5,163,979 11/1992 Patrick et al. ................ 73/23.36 X

FOREIGN PATENT DOCUMENTS 254358 10/1990 Japan ............................. 73/23.42
115972  5/1991 Japan ............................. 73/23.42
105062  4/1992 Japan ............................. 73/23.42
130269  5/1992 Japan ............................. 73/23.42

Primary Examiner—Hezron E. Williams
Assistant Examiner—Joseph W. Roskos
Attorney, Agent, or Firm—Heller, Ehrman, White & McAuliffe

[57] ABSTRACT

A gas chromatograph for operation in split mode is controlled by calculating the column flow rate and the total carrier gas flow rate from the length and inner diameter of the column and specified values for temperature and column inlet pressure, adjusting the split flow rate such that the pressure value measured by a pressure sensor becomes equal to the specified pressure value and control the total carrier flow rate to be equal to the calculated value therefor. In this manner, the split ratio of the gas chromatograph can be maintained easily at a specified value. The amount of carrier gas to be wasted can be significantly reduced by appropriately varying the split ratio with time during the course of an analysis.

9 Claims, 1 Drawing Sheet

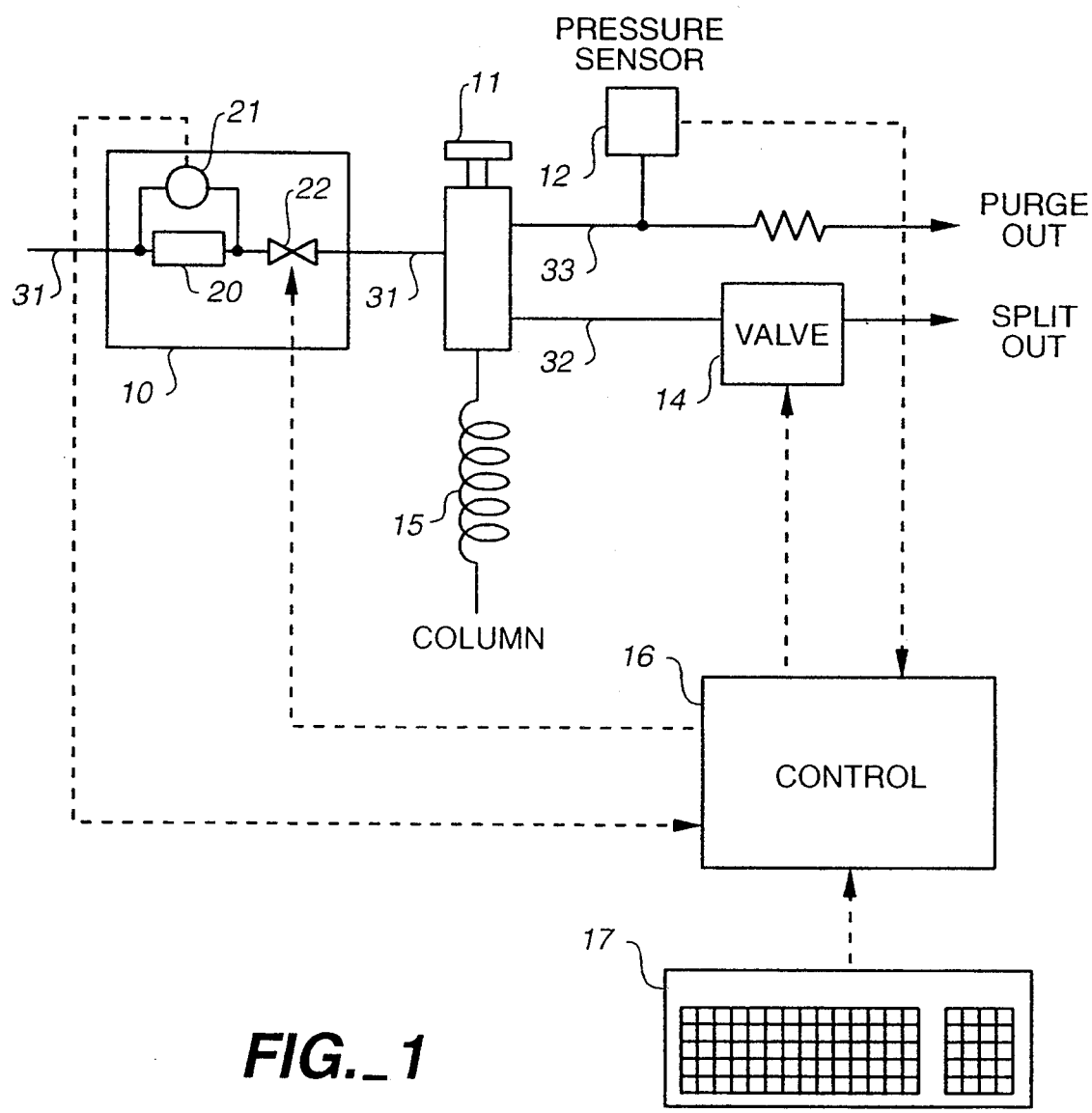
FIG._1

GAS CHROMATOGRAPH AND METHOD OF USING SAME

BACKGROUND OF THE INVENTION

This invention relates to a gas chromatograph and a method of using it in a split mode.

In conventional methods of gas chromatographic analysis in a split mode, it was necessary to separately measure the column flow rate, the split flow rate and the purge flow rate in order to adjust the split ratio to a desired value. Conventionally, the column flow rate was measured either directly by using a flow meter or calculated from a measured retention time of methane, and the split and purge flow rates were directly measured by a flow meter. Since the measurements of flow rates by such methods are troublesome, it was time-consuming to adjust the split ratio.

The present invention has been accomplished in view of this problem, and its object is to provide a gas chromatograph which allows the split ratio to be adjusted easily to a desired value.

SUMMARY OF THE INVENTION

A gas chromatograph according to the present invention, with which the above and other objects can be accomplished, may be characterized as comprising (a) carrier gas flow rate controlling means for controlling the flow rate of a carrier gas which flows into a sample injection unit; (b) a split flow rate controlling means for controlling the flow rate of the gas which is split out of the sample injection unit; (c) a pressure sensor for measuring the column inlet pressure; (d) a column flow rate calculating means for calculating the flow rate in the column from the length and inner diameter of the column, the specified values of the column temperature and the column inlet pressure; and (e) a control means for adjusting not only the split flow rate such that the measured value by the pressure sensor becomes equal to the specified value of the column inlet pressure but also the carrier gas flow rate such that the split ratio, which is defined as the ratio between the column flow rate and the split flow rate, becomes equal to a specified value.

The flow rate of a gas inside a column can be hydrodynamically calculated from the length and the inner diameter of the column, the gas temperature and the column inlet pressure, although empirical corrections may be incorporated in order to improve the accuracy. Thus, the column flow rate $U_c$ can be calculated by the aforementioned column flow rate calculating means if the column temperature specified at the time of an analysis (this temperature being considered equal to the gas temperature), data on the column inlet pressure, the length and the inner diameter of the column to be used are given. If the column flow rate $U_c$ is known and the split ratio S is specified, the total flow rate U of the carrier gas is given by $(1+S)U_c$. Thus, if the control means uses the split flow rate control means to keep the split flow rate at $SU_c$ and the measured value of the pressure sensor becomes equal to a specified value, and if the control means further uses the carrier gas flow rate controlling means to adjust the total flow rate of the carrier gas to U, the column flow rate $U_c$ becomes constant and the split ratio is maintained at the specified value S.

BRIEF DESCRIPTION OF THE DRAWINGS

FIG. 1 which is a piping diagram of a gas chromatograph embodying the present invention, is incorporated in and forms a part of this specification, and serves to explain the principles of the invention.

DETAILED DESCRIPTION OF THE INVENTION

A gas chromatograph according to one embodiment of the present invention will be described with reference to FIG. 1, wherein numeral 15 indicates a capillary column and numeral 11 indicates a sample injection unit at the inlet of the column 15. The piping system for the apparatus includes a carrier introducing line 31 for introducing a carrier gas into the sample injection unit 11, a split line 32 for discharging a portion of the sample injected into the sample injection unit 11 without delivering it into the column 15, and a purge line 33 for discharging contaminants such as substances emitted from a rubber plug into the sample injection unit 11.

The carrier introducing line 31 contains a mass flow controller 10, which is for adjusting the total carrier gas flow rate U of the carrier gas to any desired value and includes a laminar flow control 20, a differential pressure sensor 21, and a flow rate control valve 22 for detecting and adjusting the total flow rate U. The split line 32 contains a control valve 14 for controlling the split flow rate $U_s$, and the purge line 33 contains a pressure sensor 12. Since there is hardly any gas resistance between the pressure sensor 12 and the sample injection unit 11, the pressure value detected by this pressure sensor 12 may be regarded equal to the pressure inside the sample injection unit 11, that is, the column inlet pressure.

The gas chromatograph according to this embodiment of the invention is further comprised of a control unit 16. Various parameters (to be described below) inputted from a keyboard 17, or an external memory device (not shown), are used by the control unit 16 to control each component of the apparatus described above such that the split ratio becomes equal to a specified value. Before the functions of the control unit 16 for carrying out such a control are explained, however, the basic principle of controlling the split ratio according to the present invention will be described next.

The gas flow rate inside the column 15 depends on the length L and the inner diameter D of the column 15, the gas temperature T and the gas pressure P. In this situation, the gas pressure P may be represented by the pressure value at the column inlet. If the values of these variables are given, the gas flow rate $U_c$ inside, the column 15 can be calculated hydrodynamically as:

$$U_c = f(T, D, L, P) \tag{1}$$

where the function f(T, D, L, P) can be theoretically derived hydrodynamically and depending upon the physical properties of the gas being used. Such a function may be derived also by experimentally determining various coefficients of a hydrodynamically derived basic formula.

Since the physical dimensions (length, inner diameter, etc.) and temperature of the purge line 33 are constant, the flow rate therethrough (the purge flow rate) $U_p$ depends only on the gas pressure P and may be expressed as:

$$U_p = g(P) \tag{2}$$

where the function $g(P)$ can be derived in a similar manner as the aforementioned function $f(T, D, L, P)$. The split flow rate $U_s$ can be calculated from the column flow rate $U_c$ and the split ratio $S$ as:

$$U_s = SU_c. \tag{3}$$

The total carrier gas flow rate $U$ is obtained as the sum of the column flow rate $U_c$, the purge flow rate $U_p$ and the split flow rate $U_s$. Thus, $$\begin{aligned} U &= U_c + U_p + U_s \\ &= U_c + U_p + SU_c \\ &= (1 + S)f(T, D, L, P) + g(P). \end{aligned} \tag{4}$$

Thus, in order to adjust the split ratio $S$ of this apparatus to a specified value $S_0$ where the length and inner radius of the column 15, temperature and the column inlet pressure are given respectively as $L_0$, $D_0$, $T_0$ and $P_0$, the total flow rate $U$ of the carrier gas should be made equal to $U_0$ given by the following formula:

$$U_0 = (1 + S_0)f(T_0, D_0, L_0, P_0) + g(P_0). \tag{5}$$

In order to accomplish this, the control unit 16 proceeds as follows to adjust the split ratio to a specified value $S_0$. First, the operator inputs from the keyboard 17 the column temperature $T_0$, the length $L_0$ and the inner diameter $D_0$ of the column, a specified value of column inlet pressure $P_0$, and another specified value of split ratio $S_0$. On the basis of these inputted data, the control unit 16 uses Formula (1) to calculate the column flow rate $U_{c0} = f(T_0, D_0, L_0, P_0)$ and Formula (5) to calculate the total flow rate $U_0$ of the carrier gas. Next, the opening of the control valve 14 is adjusted such that the detected value of the pressure $P$ from the pressure sensor 12 will be constant at the specified value $P_0$. As a result, the purge flow rate $U_{p0} = g(P_0)$ becomes constant, making the column flow rate $U_{c0} = f(T_0, D_0, L_0, P_0)$ also constant if the temperature is constant. Thus, the split flow rate $U_s$ also becomes constant if the mass flow controller 10 is controlled such that the carrier gas flow rate is $U_0$, and the split ratio of the apparatus is kept constant at the specified value $S_0$.

According to the embodiment of the present invention described above, the split ratio can be maintained constant, even if there are gradual changes in the column temperature $T$, by sequentially carrying out the calculations described above on the basis of the temperature at each point in time to thereby update the target pressure value $P_0$ and the carrier gas flow rate $U_0$.

Since the column inlet pressure $P$ can be derived from the average linear column speed $v_m$, it may instead be required to specify an average linear column speed value $v_{m0}$ and a split ratio value $S_0$ from the keyboard 17. More generally, it is to be noted that if any one from the average linear speed $v_m$, the column inlet pressure $P$ and the purge flow rate $U_p$ is set, and if either the total flow rate $U$ or the split ratio $S$ is set, the others of these parameters are uniquely determined. In other words, any combination of one from $v_m$, $P$ and $U_p$ and either $U$ or $S$ may be specified to determine all of them.

Although it was explained above that the values $D_0$ and $L_0$ of the inner diameter and the length of the column 15 were to be inputted from the keyboard 17, this is not intended to limit the scope of the invention. According to an alternative input method, the inner diameters and the lengths of all columns that are expected to be used are preliminarily stored in the control unit 16, and the user is required only to specify a column, and the required data for the specified column are automatically read out. Similarly, standard values of column input pressure $P_0$ and split ratio $S_0$ may be preliminarily stored in the control unit 16, allowing the user to choose from such standard values. As for the column temperature $T_0$, a preferred method is to cause the temperature data to be automatically inputted into the control unit 16, for example, from the control device for analysis being carried out and in accordance with the mode of this analysis.

Next will be described a few examples of a way in which an gas chromatograph, as described above, may be used. In a first example, the apparatus is used selectably both for an split analysis and a splitless wide bore injection analysis. Conventionally, apparatus for a split analysis and those for a splitless wide bore injection analysis were separately provided. The gas chromatograph described above, however, can be used in a splitless mode by closing the control valve 14 completely and controlling the flow rate control valve 22 of the mass flow controller 10 such that the pressure value $P$ detected by the pressure sensor 12 will become equal to a specified value $P_0$. Thus, if the control unit 16 is preliminarily so programmed that a control as described above will be carried out in response to an input of zero from the keyboard 17 as the value of split ratio $S_0$, or an input of a command for a total flow analysis, the apparatus can be switched between the split and splitless modes of analysis merely by a key input.

Another example is a mode of operation in which the split ratio is intentionally varied during the course of a single analysis such that the amount of carrier gas to be wasted will be reduced. The purpose of a split is to divide into parts the sample injected into the carrier gas, and it is only the carrier gas that is split out before the sample is injected or after the sample has been sent out to the column. This means that a significant amount of the carrier gas is wasted where, for example, the split ratio is 1:100 such that the carrier gas is mostly split out. According to an embodiment of the present invention, the control unit 16 causes the split ratio $S$ to be varied during a single analysis, as will be explained next.

First, the mass flow controller 10 and the control valve 14 are controlled such that the split ratio becomes equal to a preliminarily specified value $S_0$ (such as 100), and the injection of sample is started after the flow rate has stabilized. After the sample injection is completed, the split ratio is maintained at the specified value $S_0$ for a selected length of time (such as one minute) which is longer than the time required for sending the sample into the column 15. After this selected length of time, the split ratio is changed to a reduced value $S_1$ (such as 5). In this manner, the amount of carrier gas that is split out can be significantly reduced.

With a gas chromatograph according to the present invention, troublesome operations such as the direct measurements of the column flow rate and the split flow rate are not necessary, and analyses can be carried out in a split mode with an arbitrarily specified split ratio. Moreover, a single apparatus can be used both in split and splitless modes, and the amount of wasted carrier gas can be reduced significantly by appropriately varying the split ratio during the course of an analysis.

What is claimed is:

1. A gas chromatograph operable in a split mode, comprising:

a capillary column with an inlet;

a sample injection unit at said inlet of said column;

a carrier introducing line for introducing a carrier gas into said sample injection unit, said carrier introducing line containing a carrier flow rate controlling means for controlling the total flow rate U of said carrier gas flowing into said sample injection unit;

a split piping line with one end connected to said sample injection unit;

a split flow rate controlling means for controlling split flow rate $U_s$ of a gas split out of said sample injection unit through said split piping line;

a pressure sensor for measuring pressure at said inlet of said column;

a column flow rate calculating means for calculating a column flow rate value representing column flow rate $U_c$ of said gas inside said column corresponding at least to a specified pressure value $P_0$; and a control means for adjusting said split flow rate $U_s$ in said split piping line such that measured pressure value by said pressure sensor becomes equal to said specified pressure value $P_0$, and adjusting said total flow rate U in said carrier introducing line such that split ratio S, which is the ratio of said split flow rate $U_s$ to said column flow rate $U_c$, becomes equal to a specified split ratio value $S_0$.

2. The gas chromatograph of claim 1 wherein said column flow rate calculating means calculates said column flow rate also from the length and inner diameter of said column and the temperature of said gas inside said column.

3. A method of operating a gas chromatograph, said gas chromatograph comprising:

a capillary column with an inlet;

a sample injection unit at said inlet of said column;

a carrier introducing line connected to said sample injection unit; and a split piping line with one end connected to said sample injection unit;

said method comprising the steps of:

introducing a carrier gas through said carrier introducing line into said sample injection unit at intake flow rate U to thereby cause a portion of said carrier gas to flow through said column at column flow rate $U_c$ and another portion of said carrier gas to be split out at split flow rate $U_s$ through said split piping line, split ratio being defined as the ratio between said column flow rate $U_c$ and said split flow rates $U_s$;

injecting a sample into said sample injection unit;

specifying a pressure value $P_0$ and a split ratio value $S_0$;

calculating a column flow rate value $U_{c0}$ corresponding to said pressure value $P_0$ by using a predetermined functional relationship between said column flow rate $U_c$ and pressure at said inlet of said column;

calculating an intake flow rate value $U_0$ corresponding to said pressure value $P_0$, said column flow rate value $U_{c0}$ and said split ratio value $S_0$ by using a predetermined functional relationship of said intake flow rate U with said pressure at said inlet of said column and said split ratio;

adjusting said pressure at said inlet of said column to said pressure value $P_0$; and adjusting said intake flow rate U of said carrier gas to said intake flow rate value $U_0$.

4. The method of claim 3 wherein said pressure at said inlet of said column is adjusted to said pressure value $P_0$ by adjusting the opening of a control valve provided in said split piping line.

5. The method of claim 3 wherein said intake flow rate U of said carrier gas is adjusted to said intake flow rate value $U_0$ by controlling a mass flow controller provided in said carrier introducing line.

6. The method of claim 3 wherein said steps of adjusting said pressure at said inlet of said column and said intake flow rate U of said carrier gas are repeated sequentially, such that said split ratio is maintained constant in spite of gradual changes in temperature.

7. A method of operating a gas chromatograph, said gas chromatograph comprising:

a capillary column with an inlet;

a sample injection unit at said inlet of said column;

a carrier introducing line connected to said sample injection unit; and a split piping line with one end connected to said sample injection unit;

said method comprising the steps of:

introducing a carrier gas through said carrier introducing line into said sample injection unit at intake flow rate U to thereby cause a portion of said carrier gas to flow through said column at column flow rate $U_c$ and another portion of said carrier gas to be split out at split flow rate $U_s$ through said split piping line, split ratio being defined as the ratio between said column flow rate $U_c$ and said split flow rates $U_s$;

adjusting said split ratio to a specified ratio value $S_0$;

injecting a sample into said sample injection unit;

maintaining said split ratio at said specified ratio value $S_0$ for a specified time interval after the completion of said step of injecting said sample; and thereafter reducing said split ratio significantly.

8. The method of claim 7 wherein said step of adjusting said split ratio comprises the steps of:

specifying a pressure value $P_0$;

calculating a column flow rate value $U_{c0}$ corresponding to said pressure value $P_0$ by using a predetermined functional relationship between said column flow rate $U_c$ and pressure at said inlet of said column;

calculating an intake flow rate value $U_0$ corresponding to said pressure value $P_0$, said column flow rate value $U_{c0}$ and said specified ratio value $S_0$ by using a predetermined functional relationship of said intake flow rate U with said pressure at said inlet of said column and said split ratio;

adjusting said pressure at said inlet of said column to said pressure value $P_0$; and adjusting said intake flow rate U of said carrier gas to said intake flow rate value $U_0$.

9. The method of claim 7 wherein said specified time interval is long enough to allow said injected sample to be sent into said column.

* * * * *